Figure 1:
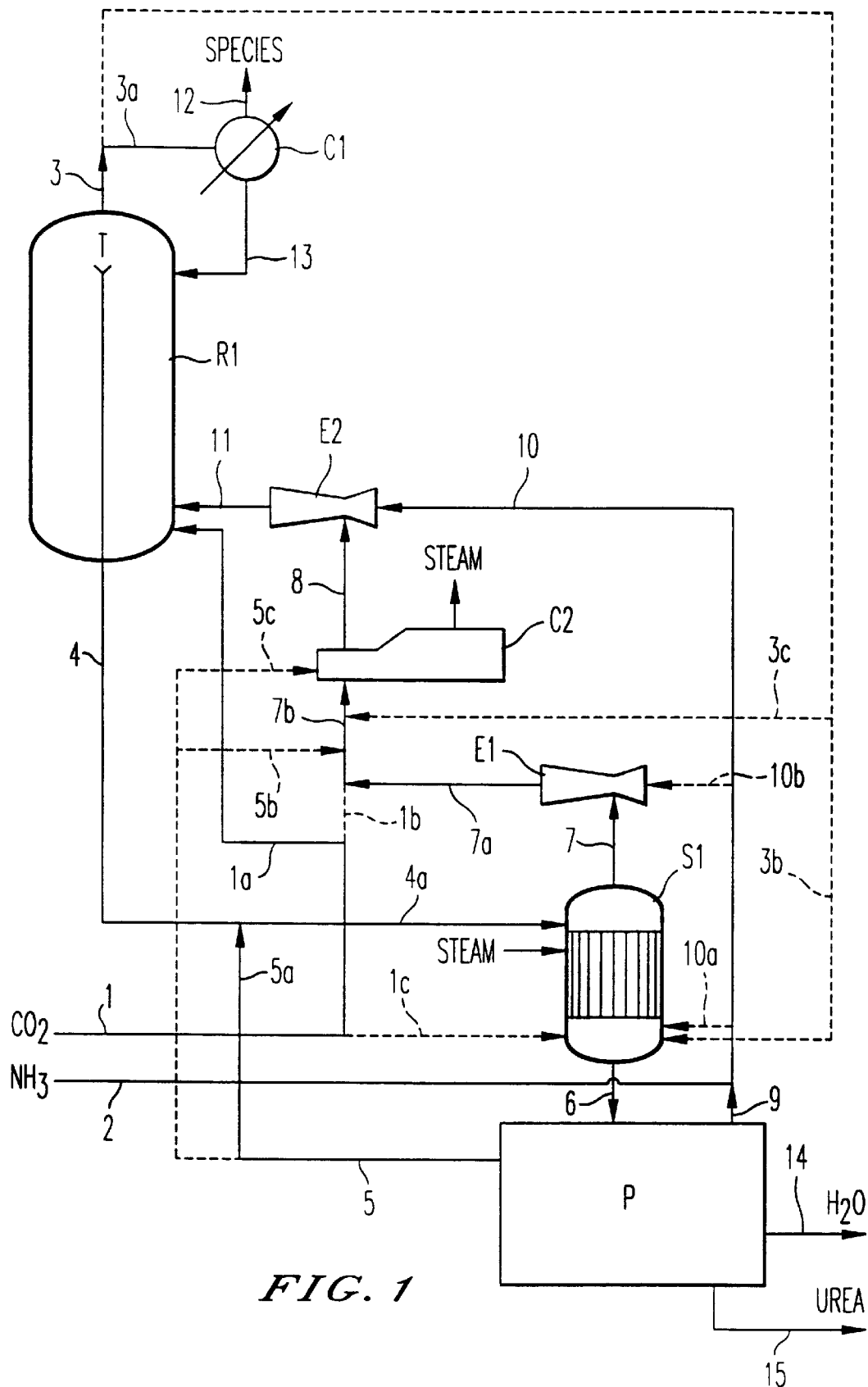

United States Patent [19]

Rescalli

[11] Patent Number: 5,886,222
[45] Date of Patent: *Mar. 23, 1999

[54] HIGH YIELD PROCESS FOR UREA SYNTHESIS

[75] Inventor: Carlo Rescalli, Milanese, Italy

[73] Assignee: Snamprogetti S.p.A., S. Donato Milanese, Italy

[*] Notice: The term of this patent shall not extend beyond the expiration date of Pat. No. 5,763,660.

[21] Appl. No.: 912,921

[22] Filed: Aug. 15, 1997

Related U.S. Application Data

[63] Continuation of Ser. No. 594,490, Jan. 31, 1996, Pat. No. 5,763,660.

[30] Foreign Application Priority Data

Feb. 16, 1995 [IT] Italy ................................. MI95/A0281

[51] Int. Cl.$^6$ ................................................. C07C 273/04
[52] U.S. Cl. ................................. 564/70; 564/67; 564/69; 564/71
[58] Field of Search ................................. 564/67, 69, 70, 564/71

[56] References Cited

U.S. PATENT DOCUMENTS

| | | | |
|---|---|---|---|
| 3,356,723 | 12/1967 | Kaaenbrood | 260/555 |
| 4,208,347 | 6/1980 | Pagani | 260/555 |
| 4,670,588 | 6/1987 | Zardi | 564/72 |
| 4,801,745 | 1/1989 | Meessen et al. | 564/70 |
| 4,801,746 | 1/1989 | Baenens | 564/70 |

FOREIGN PATENT DOCUMENTS

| | | |
|---|---|---|
| 0479103 | 4/1992 | European Pat. Off. . |
| 1538285 | 7/1968 | France . |
| 2748221 | 5/1978 | Germany . |
| 9623767 | 8/1996 | WIPO . |

*Primary Examiner*—Shailendra Kumar
*Attorney, Agent, or Firm*—Oblon, Spivak, McClelland, Maier & Neustadt, P.C.

[57] ABSTRACT

Improved yield process for urea synthesis by starting from ammonia and carbon dioxide, comprising a reaction zone under high pressure and temperature conditions, a section wherein a portion of unreacted ammonia and carbon dioxide are stripped and recycled to the reactor, which section operates under substantially the same reactor pressure, and a subsequent section, operating under medium and/or low pressure conditions, for urea purification and simultaneous recovery of residual carbon dioxide and a portion of residual ammonia contained in the effluent stream from the stripping section, as an aqueous solution of ammonium carbamate, in which said aqueous ammonium carbamate solution is either totally or partially fed to said stripping section. Said process makes it possible a conversion of carbon dioxide into urea to be obtained in the reactor which is higher than 70%.

3 Claims, 2 Drawing Sheets

HIGH YIELD PROCESS FOR UREA SYNTHESIS

This is a Continuation of application Ser. No. 08/594,490 filed on Jan. 31 1996, now U.S. Pat. No. 5,763,660.

The present invention relates to a process for high yield synthesis of urea.

In particular, the present invention relates to an improved-yield process for urea synthesis, comprising the reaction of ammonia and carbon dioxide under high temperature and pressure conditions, the following separation of urea from the mixture containing the unreacted products, and the recycle of the latter to the reactor.

All industrial processes for urea preparation are based on the direct synthesis according to the reaction:

$$2NH_3 + CO_2 \longleftrightarrow CO(NH_2)_2 + H_2O \quad (1)$$

This reaction takes place according to well distinct reaction steps:

$$NH_3 + CO_2 \longleftrightarrow (NH_2)COONH_4 \quad (1a)$$

$$(NH_2)COONH_4 \longleftrightarrow CO(NH_2)_2 + H_2O \quad (1b)$$

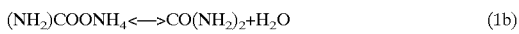

In the first step, an exothermic equilibrium reaction occurs, having a high reaction rate at room temperature, which, however, requires high pressures in order to reach a favourable equilibrium under the high temperature conditions required by (1b) step.

During the second step, and endothermic reaction takes place which reaches a meaningful rate only at high temperatures (>150° C.), with an equilibrium state which at 185° C. leads to a $CO_2$ conversion of only approximately 53% in a reaction mixture containing a stoichiometric ratio of the reactants. This unsatisfactory conversion can be advantageously increased by increasing the ratio of $NH_3:CO_2$, but is further reduced in the presence of water. The latter has furthermore an unfavourable effect also on the overall process kinetics.

Both above reaction steps are not normally carried out in separate zones of the reactor, but they occur simultaneously inside the reaction mixture, which, therefore, comprises urea, water, ammonia, carbon dioxide and ammonium carbamate, with relative concentrations in the different reactor areas, which depend on the several thermodynamic and kinetic factors which contribute to the process.

Processes for obtaining urea by direct synthesis by starting from ammonia and carbon dioxide have been widely reported and disclosed in technical literature specifically dealing with this area. A vast review of the most common processes for producing urea can be found, e.g., in "Encyclopedia of Chemical Technology" Kirk-Othmer, Ed., Wiley Interscience, third edition (1983), volume 23, pages 551–561.

The industrial processes for urea production normally perform the synthesis inside a reactor to which $NH_3$, $CO_2$, and the aqueous solutions of ammonium carbonate and/or carbamate from the unconverted reactants recycle streams are fed, at temperatures comprised within the range of from 170° to 200° C., under pressures of at least 130 atm, with a molar ratio of $NH_3:CO_2$ comprised within the range of from 2.5 to 4.5, as based on total feed streams. The molar ratio of $H_2O:CO_2$ fed to the reactor is generally comprised within the range of from 0.5 to 0.6. Under such conditions, the product discharged from the reactor shows conversion rates comprised within the range of from 50 to 65%, based on fed $CO_2$. Besides water formed and the excess of fed $NH_3$, the effluent stream from the reactor additionally contains large amounts of $CO_2$, prevailingly as unconverted ammonium carbamate.

The separation of urea from these products is carried out in a plurality of sections operating at high temperature and under decreasing pressures, inside which both the decomposition of ammonium carbamate into $NH_3$ and $CO_2$ (products made available for being recycled to the reactor), and the evaporation of reaction water take place, with high-purity urea being finally obtained which is sent to the subsequent prilling step. The carbamate separation and recycle section requires investment costs for the facilities which considerably add to the cost of the end product.

From this section, all $CO_2$ and a portion of $NH_3$, owing to their simultaneous presence, are made available for being recycled as ammonium salts (carbonate and/or hydrogen-carbonate and/or carbamate, according to temperature, imposing the use of water as solvent medium to circulate them, in order to prevent salts from precipitating and consequently blocking the concerned lines. This procedure implies an increase in water mount contained in the several liquid process streams and inside the reactor, with the consequent negative effects on conversion, as mentioned hereinabove. Known processes operating according to the above general scheme are, e.g., disclosed in U.S. Pat. No. 4,092,358; U.S. Pat. No. 4,208,347; U.S. Pat. No. 4,801,745; and U.S. Pat. No. 4,354,040.

In order to better clarify the above, we think it useful to stress that the water amount recycled to the reactor for said handling is of the order of magnitude of water amount produced during the reaction. Therefore, the traditional reactor is particularly penalized because since from the very beginning of the process, it is interested by the high water concentration coming from the recycle lines. Furthermore, the maximal water concentration is precisely found in the end reactor zone in which, on the contrary, having an as low as possible water concentration would be much more useful, in order to favour the rightwards shift of equilibrium in (1b) step, precisely in said end zone in which urea concentration is already relatively high.

In order to obviate the above said drawbacks and increase as far as possible $CO_2$ conversion into urea in traditional facilities, the operators attempted to operate under still higher temperature and pressure conditions, although such an operating mode may imply a further increase in investment and operations costs. Unfortunately, even so, conversion levels of 60–65% cannot be exceeded.

The present Applicant found now a process which makes it possible the difficulties and limitations affecting the traditional industrial processes, as mentioned above, to be overcome, with $CO_2$ conversions into urea of higher than 70% being reached.

Therefore, the object of the present invention is an improved process for urea synthesis from ammonia and carbon dioxide, with ammonium carbamate being formed as an intermediate species, which comprises the following steps:

(a) feeding ammonia and carbon dioxide to at least one reactor and causing them to react with each other, with a molar ratio of $NH_3:CO_2$, either as such, or as ammonium carbamate, comprised within the range of from 2.1 to 10, preferably of from 2.1 to 6.0, with a first liquid mixture containing urea, ammonium carbamate, water and ammonia being formed;

(b) transferring said first liquid mixture to a decomposition-stripping step;

(c) heating said first liquid mixture in said decomposition-stripping step, operating substantially under the same pressure as existing in said reactor, to cause a portion of ammonium carbamate to get decomposed into ammonia and carbon dioxide, and simultaneously submitting said liquid mixture to stripping, with a first gas mixture containing ammonia and carbon dioxide, and a second liquid mixture containing urea, water, ammonia, and the undecomposed portion of ammonium carbamate, being formed;

(d) transferring, possibly through an ejector, said first gas mixture to a condensation step substantially operating under the same reactor pressure and condensing said mixture, with a third liquid mixture being formed which contains ammonium carbamate and ammonia, which third liquid mixture is recycled, possibly through an ejector, to the reactor of the (a) step;

(e) recovering urea contained in said liquid mixture in one or more subsequent decomposition/separation step(s) with substantially pure urea, a fourth liquid mixture containing water, ammonia and ammonium carbamate and, possibly, a fifth stream substantially containing ammonia, being formed; wherein said fourth liquid mixture formed in (e) step is totally or partially, preferably from 50 to 100% thereof, combined with said first liquid mixture and is sent to said first decomposition-stripping step, with the residual portion, if any, being sent to the reactor, or, preferably, to said condensation step.

According to the process of the present invention, which is usually carried out continuously on a suitable facility, fresh ammonia and fresh carbon dioxide are continuously fed to the facility in order to compensate for (i.e., replenish) the corresponding amounts of reactants converted into urea and discharged from the end separation and prilling sections.

Fresh ammonia and fresh carbon dioxide can be directly fed to the reactor, but they are preferably at least partially used as the drive fluid for one or more ejector(s), in order to supply the necessary drive for said first gas stream discharged from the (c) stripping step, and/or ammonium carbamate coming from (d) condensation step to circulate. Ammonia is particularly preferred for use for that purpose.

According to an alternative route, or also simultaneously to the use of the ejector(s), fresh ammonia or fresh carbon dioxide can be used either totally or partially, as the stripping fluid in the stripper and/or can be directly sent to the condenser.

The synthesis reactor normally operates at temperatures comprised within the range of from 160° to 215° C., preferably comprised within the range of from 170° to 205° C., and under pressures comprised within the range of from 90 to 250 abs.atm, preferably of from 120 to 180 abs.atm, with molar ratios of ammonia:carbon dioxide preferably comprised within the range of from 2.1 to 6.0, more preferably of from 2.5 to 4.5.

The reactor is normally equipped with a plurality of trays, of a type selected from the different types known in the art, so as to realize the optimal conditions of plug flow, possibly also in the presence of two-phase systems. The reactor can also comprise a plurality of reaction zones, suitably interconnected with each other, possibly with different feed streams.

Heat developed and, more generally, the temperature level of the reactor in the (a) step is controlled by acting on the temperature level of carbon dioxide and/or ammonia stream (s) fed to the reactor and/or based on the subdivision of said feed streams between stripper, condenser and reactor and/or on the amount of heat removed in the condenser.

The reactor must display a value of liquid hold-up which will enable the residence time of said liquid inside the reactor to be comprised within the range of from a few minutes up to some ten minutes, in order to allow ammonium carbamate formed by the reaction of ammonia with carbon dioxide in the (d) condensation step and/or inside the same reactor, to undergo dehydration into urea.

In the process according to the present invention, in the (a) reaction step, also a second gas stream can be separated, as an effluent stream from reactor top, which is rich in inert species which must be removed. Such a gas stream is preferably submitted to condensation in order to recover ammonia and carbon dioxide contained in it, which are then directly recycled to the reactor. According to a second embodiment, such a gas stream is sent to the decomposition-stripping step, and the inert species are then subsequently separated from recycled carbamate stream to reactor.

In the process according to the present invention, in which the reactor is caused to operate with an excess of ammonia over the stoichiometric ratio to carbon dioxide as necessary to produce ammonium carbamate, and, then, urea (2:1, by mol), the reactor leaving stream and, generally, most liquid streams which are formed in the process, usually contain ammonia in excess. In the instant disclosure, reference is made to the composition of such liquid (or also two-phase) streams and mixtures, conventionally assuming that all carbon dioxide is present as ammonium carbamate, and any residual ammonia excess is present as free ammonia, or, more simply, ammonia.

Furthermore, in order to simplify the present disclosure, the term "liquid" is indifferently used with reference to streams or mixtures of the process according to the present invention, which are constituted either by one single liquid phase, or by a mixed liquid-vapour phase. On the contrary, the term "gas" is used for those streams or mixtures in which the liquid phase is substantially absent.

The (c) decomposition-stripping step is normally carried out in a stripper usually heated by indirect, high pressure steam. The temperature of the stripper is normally comprised within the range of from 160° to 220° C., and the pressure inside it is equal to, or slightly lower than, the pressure inside the reactor, so as to make possible the decomposition products (first gas stream) to be recycled using, as driving means, only, and possibly, ejectors.

Under the above said conditions, ammonium carbamate tends to rapidly decompose forming ammonia and carbon dioxide, and urea already formed inside the reactor remains substantially unchanged. The stripping can be carried out by using fresh ammonia or fresh carbon dioxide as the drive gases. From technical literature, different examples of processes for urea synthesis which use said principle, are described. For example, U.S. Pat. No. 3,356,723 to STAMICARBON discloses the use of carbon dioxide as stripping gas. On the other hand, G.B. patent No. 1,016,220 to SNAMPROGETTI discloses the use of ammonia in order to achieve the same purpose.

According to a preferred embodiment of the present invention, the decomposition-stripping step is carried out by using, as the drive gas, the same ammonia excess present in the reactor leaving stream. Further details on such a preferred technology can be found, e.g., in U.S. Pat. No. 3,876,696 to SNAMPROGETTI, the contents of which are incorporated hereto by reference. This last technology is referred to as "self-stripping".

According to the present invention, the decomposition-stripping step can also be carried out inside two equipment pieces (strippers) in cascade, possibly of different types from each other and operating under different conditions from each other, as disclosed, e.g., in G.B. patent 1,581,505, the contents of which are incorporated hereto by reference.

According to the present invention, from the (c) decomposition-stripping step, a first gas mixture of ammonia and carbon dioxide having a very low water content, is obtained. The water content is normally comprised within the range of from 0.0 to 10%, preferably of from 0.0 to 5.0% by weight, based on total gas mixture weight. Such a small water content is that content which is normally obtained from the high-pressure stripping steps carried out according to the processes cited above.

In general, the (c) decomposition-stripping step is carried out inside tube-bundle apparatuses with falling liquid film. The effluent mixture from the reactor, together with the fourth liquid mixture coming from the steps downstream from the stripper, is preferably fed to the head of the apparatus and forms a falling film along the walls of the tube bundle. However, also other well-known types of apparatuses can be used in the present process, which are suitable for the intended purpose.

The (d) condensation step is normally carried out inside suitable condensers, e.g., of tube-bundle or surface types, in which the condensation heat is used in order to heat other fluid streams. The condensation heat is preferably used to generate steam, but it can also be used to supply heat to one of the subsequent medium or low pressure ammonium carbamate decomposition steps.

According to the present invention, the condensation step can be carried out under the usual conditions (temperature, pressure and composition) used in the processes known from the prior art, provided that these are such as to prevent solid ammonium carbamate from forming in the condenser and/or in the outlet lines from it.

The separation of urea from ammonia and ammonium carbamate still present in the second liquid effluent stream from the decomposition-stripping step is carried out, according to the (e) step of the present process, in subsequent decomposition and separation sections, operating under medium (from 15 to 25 abs.atm) and/or low (from 3 to 8 abs.atm) pressure conditions. For the purposes of the present invention, such (e) separation step can be carried out by means of any of the methods described in the specific sector literature, which make it possible a liquid recycle stream to be obtained which contains an aqueous solution of ammonium carbamate and, possibly, also a stream which is essentially constituted by ammonia. Suitable separation-purification sections for the purposes of the present invention are, e.g., those which are schematically represented in FIGS. 1–5 of "Encyclopedia of Chemical Technology" ibid.

Urea so separated from ammonium carbamate and ammonia is generally obtained as an aqueous solution which is then submitted to an end step of vacuum dehydration (down to 0.1 abs.atm) with on the one side water, and on the other side, substantially pure urea being obtained which is then sent to normal prilling processes, and so forth.

According to the present invention, the (e) urea separation-purification step also includes the end dehydration step and the section of purification of waste effluent waters from synthesis facility. According to a preferred embodiment of the present invention, the several, either liquid or two-phase streams containing ammonium carbamate, coming from the several sub-sections of the (e) step (medium- and low-pressure carbamate decomposition, re-condensation of carbamate, urea dehydration, waste streams purification) are gathered one single recycle stream which constitutes said fourth liquid mixture which is then either totally or partially sent to the first decomposition-stripping step. According to certain modes of embodiment of urea separation and purification, however encompassed by the scope of the present invention, recycle ammonia and carbon dioxide can be present as ammonium carbonate, hydrogencarbonate or carbamate, or a mixture thereof, according to mixture temperature and pressure conditions.

The process according to the present invention makes it possible the water amount fed to the reactor to be meaningfully decreased, down to such a level as to have, at reactor inlet, a molar ratio of $H_2O:CO_2$ which is always lower than 0.3 (in which $CO_2$ inside the reactor is conventionally considered as being in carbamate form, as specified hereinabove). In such a way, a considerable general decrease is obtained also in water amount present in the reaction zone. This makes it possible urea synthesis to be carried out with particularly high conversion values, preferably comprised within the range of from 70 to 75% per each cycle, with no need for resorting to particularly complex and burdensome technical solutions in order to accomplish that result. In fact, the many advantages of the present process are surprisingly obtained by means of the adoption of the simple measure of feeding to the stripper a considerable portion of carbamate containing streams coming from the sections downstream from the same stripper, and carrying out the stripping under such conditions as to have a low water content in the separated gas stream.

The present process furthermore displays the advantage of being suitable for being easily and surprisingly carried out by supplying a small number of simple modifications to an already existing traditional facility, provided it is equipped with a high-pressure stripping step. In particular, it will be enough to modify the facility in such a way as to send to said stripping step, either totally, or partially, the recycled carbamate containing stream coming from the steps downstream from the same stripper.

Therefore, a further object of the present invention is a method for improving the yield of an existing process for urea production, which operates with a high-pressure synthesis section comprising at least one (self)stripping step, and subsequent urea purification and concentration steps, from which an aqueous ammonium carbamate solution is obtained, characterized in that said aqueous solution is either totally or partially, preferably from 50 to 100% thereof, fed to said (self)stripping step.

Figure 2:
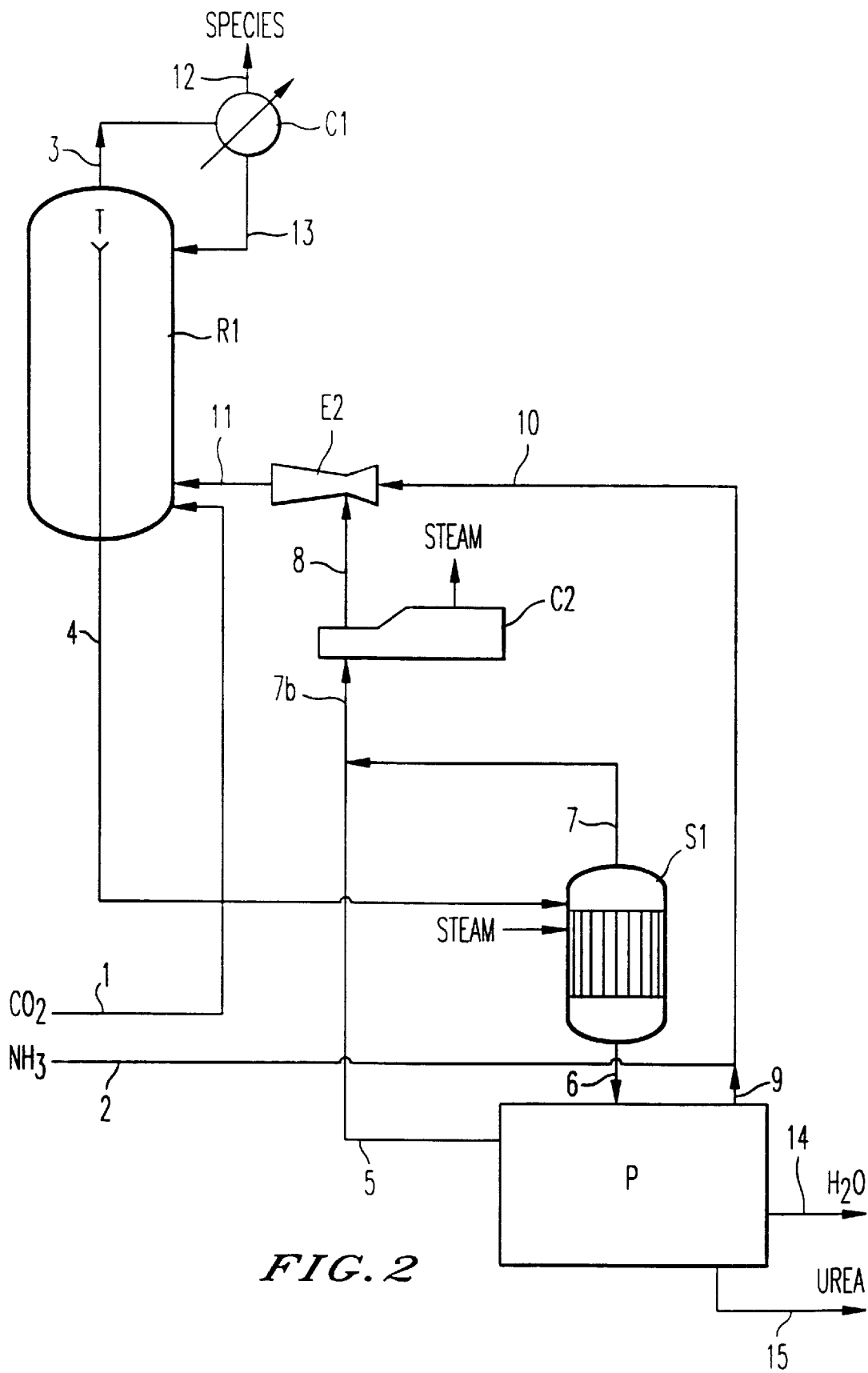

The improved process according to the present invention is further illustrated by means of two accompanying figures, in which:

FIG. 1 schematically represents the implementation of the reaction and decomposition-stripping steps (synthesis loop) of a process for urea synthesis, which constitutes a preferred embodiment of the present invention;

FIG. 2 schematically represents an analogous synthesis loop, based on a typical traditional process.

In above said FIG. 1, the dotted lines represent alternative possibilities, not mutually exclusive, available for implementing the process according to the present invention. In said figures, the functional unit, such as pumps, valves and still other pieces of equipment which are not necessary for the purpose of fully understanding the schematically shown processes, are not illustrated. In no case the process according to the present invention shall be understood as being limited to the embodiments reported and disclosed in the accompanying figures, which are supplied for merely exemplifying purposes.

In the Flow Scheme reported in FIG. 1, the reactor R1 can be seen which, through the overflow T and the line 4, is connected with the stripper S1. The latter is connected, at its bottom, with the urea separation-purification section P from which, through line 5, carbamate (line 5a) is recycled to line 4 and, possibly, (lines 5b and 5c) to the condenser C2. With the condenser C2, the stripper S1 top is connected through line 7, ejector E1, and lines 7a and 7b. The condenser outlet is represented by line 8 which is then connected with the reactor R1 through the ejector E2, to which also the line 10 comes, which conveys free ammonia (line 2) and recycled ammonia (line 9) from urea separation and purification section P. The line 1 for fresh carbon dioxide can be indifferently connected either with the reactor (line 1a) or with the condenser (line 1b) or with the stripper bottom (line 1c), or, also, with a plurality of such equipment pieces. The line 3 from the top of reactor R1 is connected with the condenser C1 (line 3a) and/or with the stripper S1 (line 3b) or the condenser C2 (line 3c).

The Flow Scheme reported in FIG. 2 substantially reproduces the same elements, with the same meaning, as contained in the Flow Scheme of FIG. 1, but with reference to a traditional process for urea synthesis. The meaningful differences relatively to FIG. 1 are constituted by the absence of line 5a, the line 5 being directly connected with the line 7–7b leading to the condenser C2, the absence of ejector E1 in the outlet line from stripper S1 top (and the corresponding absence of the drive stream 10b), fresh $CO_2$ being totally fed to the reactor, through line 1.

Referring to FIG. 1, some possibilities of embodiment of the process of the present invention are disclosed now, with anyway such a disclosure being non-limitative of the overall purview of the same invention.

Fresh ammonia, compressed and fed through line 2, is combined with recovered ammonia (line 9), coming from section P, and the resulting stream is partially sent to reactor R1 through line 10 and ejector E2, and partially to carbamate condenser C2 through ejector E1 (line 10b). According to an alternative route, as needed, ammonia can be either totally or partially fed to stripper S1 through line 10a; in this case, line 10b (and, consequently, ejector E1) can be absent. This is the case when stripping is carried out with ammonia. However, preferably, from 30 to 90% of ammonia from lines 2 and 9 is fed to the ejector E1, via 10b, with the residual portion thereof being sent to the ejector E2, via line 10.

Under usual operating conditions of the process according to the present invention, said streams 10, 10a and 10b prevailingly contain ammonia in liquid state.

Fresh $CO_2$ (line 1) can be analogously sent through lines 1a and/or 1b, according to the enthalpy requirements of reactor R1, but can also be sent, through line 1c, to stripper S1, in which case it will be also used as stripping medium.

Preferably, fresh carbon dioxide, after being compressed, is mostly directly sent to the reactor (more than 50% thereof), and partially sent to condenser C2.

The total reactor feed is constituted by streams 1a and 11, the latter with a very limited water content, partly deriving from the possible urea formation already in the ammonium carbamate condenser C2. According to the present invention, in that way the reactor preferably operates with an overall feed in which the molar ratio of water to $CO_2$ is lower than 0.2.

The liquid stream discharged from reactor R1 through the overflow T and line 4, containing urea, water, ammonia and ammonium carbamate, is sent to line 5a containing at least 50% of aqueous recovered stream coming, through line 5, from urea separation and purification section P, and is sent (line 4a) to the stripper S1. Preferably, the stream 5a contains from 70 to 100% of the recovered stream 5. The possibly residual portion of that recovery stream is sent to the condenser C2, either directly through line 5c, or indirectly through 5b.

According to a preferred embodiment of the present invention, the feed 4a to stripper S1 is subdivided into partial feed streams fed to said stripper at different levels thereof.

The gas phase present in reactor overhead is sent, through lines 3 and 3a, to the condenser C1 in which the inert species present in fresh $NH_3$ and $CO_2$ feed streams are separated; according to an alternative route, a portion of said gas phase can be sent, by means of the line 3b, to stripper S1, to act as the stripping medium, or it can be directly sent to the condenser C2 (line 3c).

The gas stream 7 discharged from stripper head, containing $NH_3$ and $CO_2$ and having a low water content, preferably lower than 10% by weight, and, still more preferably, lower than 5% by weight, is recycled to the condenser C2 (lines 7a and 7b) through the ejector E1, using $NH_3$ as the drive fluid. Here, it is condensed, under a pressure which is either equal to, or slightly lower than, the pressure existing inside the reactor, and at an as high as possible temperature, preferably higher than 150° C., in order to obtain a liquid stream (the third liquid mixture) prevailingly containing ammonium carbamate and ammonia and minor water amounts and, possibly, urea amounts. The latter is formed during the condensation step, with the operating conditions being already favourable to partially shift the preceding reported chemical equilibrium (1b) to the right. The so obtained liquid stream si fed to the reactor through line 8 and ejector E2.

The stream 6 discharged from the bottom of stripper S1, containing all produced urea, is sent to the subsequent purification and concentration steps, which are schematically combined in P section, in the Flow Scheme of FIG. 1. From here the recovered $NH_3$ and carbamate streams, already cited above, are derived, and pure urea and water are discharged through lines 15 and, respectively, 14.

In order to better illustrate the purpose and advantages of the present invention, a practical example thereof is supplied in the following, which by no way shall constitute a limitation to the scope of the claims.

In the following examples, the compositions of the several streams are reported by referring to the basic components urea, ammonia, carbon dioxide and water, independently on carbon dioxide, in those liquid streams which contain ammonia, substantially being in ammonium carbamate form.

EXAMPLE 1

A process for urea synthesis is operated by feeding to the stripper the recovery stream coming from urea separation/purification section (synthesis loop according to the present invention). Reference is made to the Flow Scheme reported in FIG. 1.

From lines 1a, 1b and 2 respectively, fresh streams of 45,461 Kg/h and 8,573 kg/h of $CO_2$ and 41,753 kg/h of $NH_3$, containing a total amount of 636 kg/h of inerts, are fed to reactor R1.

The reactor operates under 157 abs.atm and 188° C., the condenser C2 operates under 152 abs.atm and at approximately 155° C.

From the purification/concentration section P downstream of the stripper S1, an aqueous stream 5 rich in carbamate is recovered, which is constituted, in particular, by:

$H_2O$=17,181 kg/h
$CO_2$=9,415 Kg/h
$NH_3$=19,401 kg/h
Total stream 45,997 kg/h
which is totally sent again back to stripper S1 through lines 5a and 4a, after being combined with the effluent stream 4 from the reactor.

From the same section P a stream of neat $NH_3$ is simultaneously recovered through line 9 and is then combined with fresh ammonia coming from line 2.

From the total $NH_3$ stream thus obtained, 20,793 kg/h are sent, through line 10b and ejector E1, to condenser C2, and 41,753 kg/h are sent to the reactor through line 10 and ejector E2.

The total stream fed to the reactor R1 through line 11 is as follows:
$CO_2$=72,973 Kg/h
$NH_3$ 96,241 kg/h
Urea=960 kg/h (formed in C2 and equivalent to 704 and 455 kg/h of $CO_2$ and $NH_3$, respectively)
$H_2O$=288 Kg/h
Inerts=636 Kg/h
Total
stream 171,098 kg/h The liquid stream 4 discharged from reactor overflow T contains all produced urea, and, in particular, is characterized by:
Urea 73,682 Kg/h
$H_2O$=22,105 kg/h
$CO_2$=19,643 Kg/h
$NH_3$=55,032 kg/h The reactor overhead gas stream 3 is totally sent to condenser C1, allowed to operate at 75° C.; from this, a stream is discharged which contains the amount of 636 kg/h of inerts originally contained in the feed to the reactor, besides negligible amounts of $NH_3$ and $CO_2$, not taken into consideration in the above balance.

The stream 4 is sent to the stripper S1, through line 4a, after being combined with stream 5a; the stripper operates under 148 abs.atm, with a bottom temperature of 205° C., with no feed of stripping gas (self-stripper).

From the head of the stripper S1 a gas stream is discharged which is substantially free from water and is characterized by the following composition:
$CO_2$=19,643 Kg/h
$NH_3$=34,239 kg/h From stripper bottom a liquid stream 6 is discharged, which is constituted by:
Urea=73,682 Kg/h
$H_2O$=39,286 kg/h
$CO_2$=9,415 Kg/h
$NH_3$=40,194 kg/h
Total
stream 162,532 Kg/h
which is sent to the following steps of urea purification and concentration. These are substantially constituted, in this particular case, by the typical medium- and low-pressure separation sections, and by the concentration section which characterize the traditional SNAMPROGETTI urea process the general scheme of which is reported, e.g., on page 561 of "Encyclopedia of Chemical Technology", ibid.

The process for urea synthesis exemplified above is characterized by a conversion of $CO_2$ into urea, i.e. by a molar ratio of (produced urea):(total $CO_2$ fed) of 0.73. The liquid stream discharged from the stripper and sent to the subsequent urea separation/purification section is characterized by a molar ratio of urea:$CO_2$=5.74.

EXAMPLE 2

(Comparison example)

A process for urea synthesis operates with the recovered stream from urea separation/purification section (traditional synthesis loop) being fed to the high-pressure condenser. Reference is made to the Flow Scheme reported in FIG. 2.

The reactor R1, the condenser C2 and the stripper S1 (self-stripper) operate under temperature and pressure conditions which are exactly the same as of the preceding Example 1.

The reactor R1 is fed with:
(a) a fresh $CO_2$ stream through line 1;
(b) a liquid stream, through line 8, constituted by an aqueous solution containing carbamate and ammonia, recovered from urea separation/purification section P, and from stripper S1 through the condenser C2, which is driven by means of an ejector E2 using $NH_3$ as the drive fluid.

The total feed to the reactor is:
$CO_2$=73,677 Kg/h
$NH_3$=96,785 kg/h
$H_2O$=17,181 Kg/h
Inerts=636 Kg/h
Total
stream 188,279 kg/h In particular:
(a) the fresh $CO_2$ stream is constituted by 45,461 kg/h;
(b) the fresh $NH_3$ stream is constituted by 35,148 kg/h; the stream of $NH_3$ recovered as such from P, is constituted by 23,573 kg/h;
(c) the liquid stream recovered from P is constituted by:
$H_2O$=17,181 kg/h
$CO_2$=28,216 kg/h
$NH_3$=38,064 kg/h Thus, to the system consisting of the condenser C2 and reactor R1, total amounts of $NH_3$ and $CO_2$ are fed, which are equivalent to those as of the preceding example, but, in this case, with the ratio of $H_2O$:$CO_2$ being increased up to 0.57 owing to the recycle of the aqueous stream 5 to the condenser. Summarizing, the reactor R1 operates, in that case, under operating conditions equal to those as of the preceding Example 1, except for the larger amount of water deriving from the stream from condenser C2.

The stream discharged from said reactor through the overflow is constituted by:
Urea=62,291 Kg/h
$H_2O$=35,868 kg/h
$CO_2$=27,797 Kg/h
$NH_3$ 61,487 kg/h
Inert species=636 kg/h
Total effluent=188,279 Kg/h This stream is sent to the stripper S1 through the line 4.

The gas stream 7 discharged from the head of the stripper is directly sent to the condenser C2. The liquid stream 6 discharged from stripper bottom and containing all produced urea, is sent to the subsequent purification/concentration section P, which also allows excess $NH_3$ and carbamate, still present in the same stream, to be recycled through lines 5 and 9.

The traditional synthesis loop taken into consideration in this comparison example is characterized by a conversion of $CO_2$ into urea, i.e., by a molar ratio of (produced urea):(total fed $CO_2$) of 0.62. The liquid stream discharged from the stripper and sent to the subsequent separation/purification steps is characterized by a molar ratio of urea:$CO_2$=4.84.

From a comparison between the conversion values which characterize the process according to the present invention, as disclosed in Example 1, and a typical traditional process for urea synthesis, a very meaningful increase in conversion rate clearly appears (with all the other factors possibly playing a role being the same), and consequently of the production capacity of the facility, which is increased by approximately 20%.

It is furthermore evidenced that the decrease in water level circulating through the condenser-reactor loop of the present invention also allows the reactor size to be appreciably reduced, thanks to the more favourable kinetics of the same reaction.

Obviously, a large number of changes and modifications can be supplied to the process as disclosed above, which shall anyway be regarded as being fully encompassed by the purview of the present invention.

I claim:

1. Process for urea synthesis from ammonia and carbon dioxide, with ammonium carbamate being formed as an intermediate species, which comprises the following steps:

(a) feeding ammonia and carbon dioxide to at least one reactor and causing them to react with each other, with a molar ratio of $NH_3:CO_2$, either as such, or as ammonium carbamate, comprised within the range of from 2.1 to 10, with a first liquid mixture containing urea, ammonium carbamate, water and ammonia being formed;

(b) transferring said first liquid mixture to a decomposition-stripping step;

(c) heating said first liquid mixture in said decomposition-stripping step, operating substantially under the same pressure as existing in said reactor, to cause a portion of ammonium carbamate to get decomposed into ammonia and carbon dioxide, and simultaneously submitting said liquid mixture to stripping, with a first gas mixture containing ammonia and carbon dioxide, and a second liquid mixture containing urea, water, ammonia, and the undecomposed portion of ammonium carbamate, being formed;

(d) transferring, said first gas mixture to a condensation step substantially operating under the same reactor pressure and condensing said mixture, with a third liquid mixture being formed which contains ammonium carbamate and ammonia, which third liquid mixture is recycled, to the reactor of the (a) step;

(e) recovering urea contained in said liquid mixture in one or more subsequent decomposition/separation step(s) with substantially pure urea, a fourth liquid mixture containing water, ammonia and ammonium carbamate and, a fifth stream substantially containing ammonia, being formed;

characterized in that said fourth liquid mixture formed in (e) step is totally or partially, preferably from 50 to 100% thereof, combined with said first liquid mixture and is sent to said first decomposition-stripping step, with the residual portion, if any, being sent to the reactor, or, to said condensation step.

2. The process of claim 1, wherein carbon dioxide is fed to said reactor in step (a) and said gas mixture in said condensation step (d), and wherein more than 50% of said fed carbon dioxide is fed to said reactor in step (a).

3. The process of claim 1 or 2, wherein a gas phase is separated as a gas stream from a top of said reactor in step (a), and is fed, as a stripping medium, to said first liquid mixture in said decomposition-stripping step (c).

* * * * *